United States Patent
Snyder et al.

(10) Patent No.: US 10,392,500 B2
(45) Date of Patent: Aug. 27, 2019

(54) COMPOSITIONS AND METHODS FOR LIQUID MIXING ASSESSMENT

(71) Applicant: Siemens Healthcare Diagnostics Inc., Tarrytown, NY (US)

(72) Inventors: Jason Snyder, Newark, DE (US); Richard H. Carter, Jr., Merion Station, PA (US); Patricia Nichols, Milton, DE (US); William D. Dunfee, Newark, DE (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 16/050,666

(22) Filed: Jul. 31, 2018

(65) Prior Publication Data

US 2018/0334552 A1    Nov. 22, 2018

Related U.S. Application Data

(63) Continuation of application No. 14/409,104, filed as application No. PCT/US2013/047518 on Jun. 25, 2013, now abandoned.

(60) Provisional application No. 61/665,016, filed on Jun. 27, 2012.

(51) Int. Cl.
| | | |
|---|---|---|
| *C08L 5/00* | (2006.01) | |
| *C09B 67/44* | (2006.01) | |
| *C08K 5/053* | (2006.01) | |
| *C08K 5/41* | (2006.01) | |
| *G01N 35/00* | (2006.01) | |

(52) U.S. Cl.
CPC .............. *C08L 5/00* (2013.01); *C08K 5/053* (2013.01); *C08K 5/41* (2013.01); *C09B 67/0083* (2013.01); *G01N 35/00663* (2013.01); *G01N 2035/00673* (2013.01)

(58) Field of Classification Search
CPC ....................................................... C08L 5/00
USPC ........................................................ 436/166
See application file for complete search history.

(56) References Cited

U.S. PATENT DOCUMENTS

| | | |
|---|---|---|
| 5,910,288 A | 6/1999 | Schembri |
| 6,022,908 A | 2/2000 | Ma et al. |
| 6,054,122 A | 4/2000 | MacPhee et al. |
| 6,506,240 B2 | 1/2003 | Takemoto et al. |
| 6,979,365 B2 | 12/2005 | Tsuru et al. |
| 7,479,179 B2 | 1/2009 | Szajewski |
| 7,824,701 B2 | 11/2010 | Binette et al. |
| 8,003,405 B2 | 8/2011 | Albert et al. |
| 2007/0161114 A1 | 4/2007 | Curtis et al. |
| 2008/0012929 A1 | 1/2008 | Fujie et al. |
| 2009/0038701 A1 | 2/2009 | Delmotte |
| 2009/0250664 A1 | 10/2009 | Curtis et al. |
| 2009/0251681 A1 | 10/2009 | McNally et al. |

FOREIGN PATENT DOCUMENTS

WO    2010078942 A2    7/2010

OTHER PUBLICATIONS

International Search Report and Written Opinion of International Application No. PCT/US2013/047518 dated Nov. 29, 2013.
Supplementary European Search Report and Written Opinion of European Application No. EP 13808640 dated Feb. 1, 2016.
European Decision to Grant of European Application No. EP 13808640 dated Apr. 20, 2018.
Levent Bayindirli, "Density and Viscosity of Grape Juice as a Function of Concentration and Temperature", Apr. 1993, Journal of Food Processing & Preservation, vol. 17, No. 2, pp. 147-151.
Zuritz et al., "Density, viscosity and coefficient of thermal expansion of clear grape juice at different soluble solid concentrations and temperatures", Nov. 2005, Journal of Food Engineering, vol. 71, No. 2, pp. 143-149.

*Primary Examiner* — Christopher Adam Hixson
*Assistant Examiner* — Emily R. Berkeley
(74) *Attorney, Agent, or Firm* — Cynthia G. Tymeson

(57) ABSTRACT

Compositions include an aqueous solution of an organic dye of molecular weight in the range of about 300 to about 1,000 and a density-enhancing material. An amount of the density-enhancing material in the aqueous solution is sufficient to achieve a density of about 1.0 to about 1.3 g/mL. The composition has a viscosity of about 3.5 to about 5.0 centipoise. The compositions are useful in assessing the adequacy of a liquid handling mixing device to mix a reaction mixture.

12 Claims, No Drawings

COMPOSITIONS AND METHODS FOR LIQUID MIXING ASSESSMENT

This is a continuation application U.S. Ser. No. 14/409,104, filed Dec. 18, 2014 which claims the benefit of US National Stage of International Application No. PCT/US2013/047518, filed Jun. 25, 2013 and claims priority under 35 U.S.C. 119(e) to U.S. Provisional Application No. 61/665,016, filed Jun. 27, 2012. All of the applications are incorporated by reference herein in their entirety.

BACKGROUND

This invention relates to compositions, methods and kits for assessing a level of mixing of liquid reagents.

High-volume automated liquid handling devices can process hundreds to thousands of reactions per hour. These systems must maintain acceptable reaction mixing conditions to properly capture the rate of chemical reactions and/or extent of macromolecular interactions. If a reaction mixture is not sufficiently mixed, an erroneous, yet believable, result could be produced.

There is a need for a rapid, convenient and direct assessment of a level of mixing of liquid reagents, particularly on high-volume automated liquid handling devices.

SUMMARY

Some examples in accordance with the principles described herein are directed to a composition comprising an aqueous solution of an organic dye of molecular weight in the range of about 300 to about 1,000 and a density-enhancing material. An amount of the density-enhancing material in the aqueous solution is sufficient to achieve a density of about 1.0 to about 1.3 g/mL. The composition has a viscosity of about 3.5 to about 5.0 centipoise.

Some examples in accordance with the principles described herein are directed to a composition comprising an aqueous solution of an aromatic azo dye of molecular weight in the range of about 300 to about 1,000 and a monosaccharide or disaccharide. An amount of monosaccharide or disaccharide in the aqueous solution is sufficient to achieve a density of about 1.1 to about 1.2 g/mL. The composition has a viscosity of about 3.5 to about 5.0 centipoise.

Some examples in accordance with the principles described herein are directed to a method of assessing the adequacy of a test mixing device to mix a reaction mixture. A layer of water is formed in a container adjacent a layer of a composition comprising an aqueous solution of an aromatic azo dye of molecular weight in the range of about 300 to about 1,000 and a density-enhancing material. An amount of density-enhancing material in the aqueous solution is sufficient to achieve a density of about 1.0 to about 1.3 g/mL. The composition has a viscosity of about 3.5 to about 5.0 centipoise. The layers are subjected to mixing using the test mixing device at a predetermined intensity level and duration. A first absorbance from the mixture is measured at a predetermined wavelength. The mixture is subjected to mixing using a control mixing device at an intensity level and duration that maximizes mixing of the mixture and a second absorbance from the mixture is measured at the predetermined wavelength. A ratio of the first absorbance to the second absorbance is determined and a ratio less than about 1 indicates that the ability of the test mixing device to mix a reaction mixture at the predetermined intensity level and duration is not adequate.

DETAILED DESCRIPTION OF SPECIFIC EMBODIMENTS

Compositions

Examples of compositions in accordance with the principles described herein are useful in a rapid technique to identify less than acceptable mixing of reagents by liquid handling mixing devices including automated liquid handling mixing devices, thereby assessing mixing performance of the liquid handling devices. The phrase "less than acceptable mixing" refers to an extent of mixing that is less than that necessary to achieve a desired extent of a reaction such as, for example, that necessary to achieve an accurate assay for an analyte of interest. Such compositions are substantially free from reagents that might pose a health and/or safety threat to a handler of the compositions. Thus, the compositions are substantially free from substances that are carcinogenic or that require one or more of risk and safety statements, hazard statements, and hazard pictograms, and are listed as Substances of Very High Concern by the European Union Registration, Evaluation, Authorisation and Restriction of Chemicals, for example.

Some examples in accordance with the principles described herein are directed to a composition comprising an aqueous solution of an organic dye and a density-enhancing material. The organic dye is soluble in water or an aqueous medium, which means that the organic dye exhibits a solubility (weight to volume) in water or in an aqueous medium at ambient temperature and pressure of at least 90%, or at least 91%, or at least 92%, or at least 93%, or at least 94%, or at least 95%, or at least 96%, or at least 97%, or at least 98%, or at least 99%, or at least 99.5%, or at least 99.6%, or at least 99.7%, or at least 99.8%, or at least 99.9%, or 100%, for example.

The organic dye should absorb light in the visible range and be stable or resistant to decay. In some examples, the organic dye exhibits a specific absorbance wavelength in the range of about 350 nm to about 800 nm, or about 350 nm to about 700 nm, or about 350 nm to about 625 nm, or about 450 nm to about 625 nm, or about 550 nm to about 625 nm, for example. The organic dye should exhibit low toxicity, which means that the organic dye should not require one or more of risk and safety statements, hazard statements, and hazard pictograms, and should not be listed as a Substances of Very High Concern by the European Union Registration, Evaluation, Authorisation and Restriction of Chemicals, for example. The organic dye should function with a density-enhancing material discussed below.

The molecular weight of the organic dye is in the range of about 300 to about 1,000, or about 300 to about 900, or about 300 to about 800, or about 300 to about 700, or about 300 to about 600, or about 300 to about 500, or about 300 to about 400, or about 400 to about 1,000, or about 400 to about 900, or about 400 to about 800, or about 400 to about 700, or about 400 to about 600, or about 400 to about 500, or 500 to about 1,000, or about 500 to about 900, or about 500 to about 800, or about 500 to about 700, or about 500 to about 600, for example. In some examples, the organic dye is a triarylmethane dye or an azo dye, for example, an aromatic azo dye. The term "aryl" means an organic radical derived from an aromatic hydrocarbon by the removal of one atom and containing one or more aromatic rings, usually one to four aromatic rings. Examples include, by way of illustration and not limitation, a single aromatic ring such as, e.g., phenyl (from benzene), and multiple aromatic rings which are fused such as, e.g., naphthyl (from naphthalene), phenanthryl (from phenanthrene), and anthracyl (from anthracene), for example. One or more of the aromatic rings may comprise one or more substituents that provide for delocalization of electrons over the aromatic rings. Examples of such substituents include, but are not limited to, amino, sulfonate, and imino, for example.

Triarylmethane dyes may be represented by the formula: $(Ar)_3$-C—R wherein Ar may be the same or different and is aryl or substituted aryl, and R is an internal bond resulting from one of the aryl groups or a substituent on one of the substituted aryl groups, where the substituent may or may not be one that provides for delocalization of electrons over one or more aromatic rings of one or more of the aryl groups. The phrase "substituted aryl" refers to an aryl group that has one or more hydrogen atoms of one or more aromatic rings or fused aromatic rings replaced by another atom, which may be a single atom such as a halogen (chlorine, bromine, fluorine or iodine) or part of a group of atoms, which may be a group of atoms forming a functionality such as, for example, a substituent that provides for delocalization of electrons over one or more aromatic rings of one or more of the aryl groups as discussed above, or a heteroatom of a functional group such as, for example, hydroxy, or alkoxy, or a heteroatom of a group that imparts water solubility such as, for example, sulfonate, sulfate, phosphate, amidine, phosphonate, carboxylate, hydroxyl, amine, ether, or amide. For substitutions on a phenyl ring or a fused aryl ring, the substituents may be in any orientation (i.e., ortho, meta or para). The term "heteroatom" refers to oxygen, nitrogen, sulfur, or phosphorus, for example.

Azo dyes may be represented by the formula: R'—N═N—R" wherein R' and R" are independently aryl or substituted aryl. The aryl may be monoaryl (e.g., phenyl), diaryl (e.g., diphenyl), or triaryl (e.g., triphenyl). In some examples, one of R' or R" may be triarylalkyl such as, for example, triarylmethyl (e.g., triphenylmethyl), which results in a triarylmethane azo dye, for example.

In some examples in accordance with the principles described herein, the organic dye is, by way of illustration and not limitation, Erioglaucine, Ponceau S, Allura Red, Acid Red, Malachite Green, Amaranth, and salts of any of the above, for example.

In some examples, the organic dye is present in the composition in an amount that is sufficient to provide an absorbance reading that is large enough that an absorbance reading device such as, for example, a spectrophotometer, can obtain an accurate and reproducible absorbance reading from the composition after the composition is fully mixed with the water layer. The amount of organic dye in the composition is dependent, for example, on one or more of the nature of the organic dye, the nature of the density-enhancing material, and the nature of the mixing device. In some examples, the organic dye is present in the composition in an amount of about 0.005% to about 0.020%, or about 0.010% to about 0.018% (by weight) (g/mL).

Compositions in accordance with the principles described herein also contain a density-enhancing material. The density-enhancing material is a substance that increases the density of the aqueous medium comprising the organic dye. The nature of the density-enhancing material depends on one or more of the nature of the organic dye and the nature of the analyzer, for example. The nature of the organic dye and the nature of the density-enhancing material are such that the organic dye remains in solution in an aqueous medium that has a density in accordance with the principles described herein.

In some examples in accordance with the principles described herein, the density-enhancing material is a polyhydroxy compound. In some examples, the polyhydroxy compound is a monosaccharide or a disaccharide. In some examples, the monosaccharide or disaccharide is selected from the group consisting of sucrose, fructose, trehalose, sucrose, and a mixture of two or more thereof. In some examples, the polyhydroxy compound is a polyol having 3 to 10 carbon atoms, or 3 to 9 carbon atoms, or 3 to 8 carbon atoms, or 3 to 7 carbon atoms, or 3 to 6 carbon atoms, or 3 to 5 carbon atoms, or 3 to 4 carbon atoms and 2 to 10 hydroxy groups, or 2 to 9 hydroxy groups, or 2 to 8 hydroxy groups, or 2 to 7 hydroxy groups, or 2 to 6 hydroxy groups, or 2 to 5 hydroxy groups, or 2 to 4 hydroxy groups, or 2 to 3 hydroxy groups, for example. In some examples in accordance with the principles described herein, the polyol is glycerol, for example.

The density-enhancing material should impart a density to the composition such that the composition in accordance with the principles described herein will form a separate layer when placed in contact with a layer of water and the layers will stay separated until subjected to mixing. However, the composition in accordance with the principles described herein should not be so dense that components of the composition fall out of solution or that a liquid handling mixing device cannot handle the composition such as, e.g., the inability of the composition to be subjected to pipetting in a liquid handling device, for example. The density-enhancing material is present in the aqueous medium in an amount to achieve a density that is great enough so that a layer comprising the density-enhancing material remains separated from a water layer until a sufficient mix intensity is applied to the reaction, but not so great that the composition in accordance with the principles described herein cannot be handled by the mixing device on which it is used. In some examples in accordance with the principles described herein, the density-enhancing material is present in the aqueous solution in an amount sufficient to achieve a density of about 1.0 to about 1.3 g/mL, or about 1.0 to about 1.2 g/mL, or about 1.0 to about 1.1 g/mL, or about 1.1 to about 1.3 g/mL, or about 1.1 to about 1.2 g/mL. In some examples in accordance with the principles described herein, the composition has a viscosity of about 3.5 to about 5.0 centipoise, or about 3.5 to about 4.5 centipoise, or about 3.5 to about 4.0 centipoise, or about 4.0 to about 5.0 centipoise, or about 4.0 to about 4.5 centipoise.

In some examples in accordance with the principles described herein, the composition may include one or both of a buffer and a preservative. The pH of the composition in accordance with the principles described herein is in the range of about 4 to about 11, or in the range of about 4 to about 10, or in the range of about 4 to about 9, or in the range of about 4 to about 8, or in the range of about 4 to about 7, or in the range of about 4 to about 6, or in the range of about 5 to about 6, or in the range of about 5 to about 7, for example. Various buffers may be used to achieve the desired pH and maintain the pH during the mixing. Illustrative buffers include, but are not limited to, acetate, borate, phosphate, carbonate, tris, barbital, PIPES, HEPES, MES, ACES, MOPS, BICINE, ethylenediaminetetraacetate (EDTA) and combinations of two or more thereof, for example. The particular buffer employed is not critical, but in a composition for a particular mixing device one or another buffer may be preferred. The amount of buffer in the aqueous medium is that sufficient to achieve the desired pH.

The medium may also comprise one or more preservatives such as, but not limited to, sodium azide, neomycin sulfate, PROCLIN® 300, PROCLIN® 950, and streptomycin, for example. Any of the above materials, if employed, is present in a concentration or amount sufficient to achieve the desired preservative effect or function. In some examples, the preservative is present in the composition in an amount (weight to volume) of about 0.5% to about 2.0%, or about 0.7% to about 1.3% (by weight).

Methods Employing Compositions

As mentioned above, some examples in accordance with the principles described herein are directed to methods of assessing the adequacy of a test mixing device to mix a reaction mixture. The phrase "assessing the adequacy of a test mixing device" means determining whether the mixing achieved by the test mixing device at a predetermined intensity level and duration is sufficient for a particular application such as, for example, for conducting a chemical reaction including, for example, an assay for an analyte. The phrase "test mixing device" refers to a mixing device for which the adequacy of mixing is in question or is to be tested.

The mixing device may be automated, semi-automated, or non-automated and may be a separate device or part of a larger apparatus for which mixing of liquid reagents is required. The larger apparatus may comprise at least one mixing device, or at least two mixing devices, or at least three mixing devices up to a maximum of about 1000 or more mixing devices, or a maximum of about 500 mixing devices, or a maximum of about 400 mixing devices, or a maximum of about 300 mixing devices, or a maximum of about 200 mixing devices, or a maximum of about 100 mixing devices. In some examples in accordance with the principles described herein, the mixing device is part of an automated analyzer for one or both of the detection and quantitation of one or more analytes or substances of interest. As mentioned above, high-volume automated liquid handling devices can process hundreds to thousands of reactions per hour. These systems must maintain acceptable reaction mixing conditions to properly capture the rate of chemical reactions and/or extent of macromolecular interactions.

In accordance with the methods described herein, a layer of water is formed adjacent a layer of a composition as described above in, for example, a container. The term "adjacent" means that the layers share at least one boundary surface such as, for example, a layer of water on top of a layer of the composition, or a layer of the composition on top of a layer of water. In some examples, water is dispensed to a container and then the composition is dispensed in such a manner that a layer of water sits above a layer of the composition. The volume of water employed is dependent on one or more of the nature of the container, the nature of the mixing device, and the amount of the composition employed, for example. The volume of water is that which is sufficient to produce an acceptable level of absorbance after the composition is fully mixed with the water layer. The phrase "acceptable level of absorbance" means an absorbance reading that is large enough that an absorbance reading device such as, for example, a spectrophotometer, can obtain an accurate and reproducible absorbance reading from the composition after the composition layer and the water layer are mixed with a mixing device. In some examples, for a container that has a total volume of about 150 μL, the volume of water is about 120 μL to about 145 μL, or about 130 μL to about 140 μL, for example. The volume of the composition employed is dependent on one or more of the nature of the container, the nature of the mixing device, and the amount of water employed, for example. The volume of composition is that which is sufficient to produce acceptable level of absorbance after the layer comprising the composition is fully mixed with the water layer. In some examples, for a container that has a total volume of about 150 μL, the volume of composition is about 2 μL to about 20 μL, about 4 μL to about 10 μL, for example. In some examples, the amount of water is about 10 to about 50 times, or about 10 to about 40 times, or about 10 to about 30 times, or about 10 to about 20 times, or about 20 to about 50 times, or about 20 to about 40 times, or about 20 to about 30 times greater than the amount of composition.

The container may be any suitable container for containing liquids. In some examples, the container is one that is employed by a mixing device and is typically sealed at one end. The container may have any convenient cross-sectional shape such as, for example, square, rectangular, oval, or circular. The container may be, but is not limited to, a cuvette or a microtiter plate, for example. The container employed in each mixing step may be the same container or they may be different containers. If different containers are employed, the containers should have the same or similar properties with regard to the ability to read absorbance of a liquid in the container by a device for reading absorbance.

The layers in the container are subjected to mixing using the test mixing device at a predetermined intensity level and duration. The phrase "predetermined intensity level and duration" means an intensity level and a duration that under typical or normal circumstances would result in complete mixing of the composition layer and the water layer. The phrase "complete mixing" means that a homogeneous mixture or solution is formed from the layers as a result of mixing. After such mixing, a first absorbance from the mixture is measured at a predetermined wavelength and at a predetermined point of observation on the container. The predetermined wavelength is a wavelength of absorbance of the organic dye and may be the peak (maximum) absorbance wavelength. The "predetermined point of observation on the container" is that point which is sufficiently above the bottom of the container such that it is above the layer comprising a composition in accordance with the principles described herein but below the top surface of the water layer. In some examples, the predetermined point of observation on the container is that point just above the upper surface of the bottom layer of liquid, which in many examples is a composition in accordance with the principles described herein.

In accordance with the methods described herein, a layer of water adjacent a layer of a composition as described above in a container is subjected to mixing using a control mixing device. As mentioned above, the container may be the same container as the container used in the mixing discussed above employing the test mixing device or the container may be a different container. In some examples in accordance with the principles described herein, the contents of the container used in mixing with the test mixing device may be employed in the second mixing step using the control mixing device. That is, the container containing the layers that were mixed using the test mixing device may be employed for mixing with the control mixing device. The layers are subjected to mixing using a control mixing device at an intensity level and duration that is known to achieve complete mixing of the layers. After such mixing, a second absorbance is measured from the mixture at the predetermined wavelength and at a predetermined point of observation on the container. The predetermined wavelength and the predetermined point of observation are those employed in the measuring of the first absorbance. The phrase "control mixing device" refers to a mixing device that is known to working sufficiently enough to produce complete mixing of the layers.

The temperature during mixing is the temperature at which mixing is conducted on a particular mixing device. The temperature of mixing is dependent on one or more of the nature of the mixing device, the nature of the composition, the nature of the reactions, and the nature of the analyzer, for example. In some examples, for a mixing device that is part of an assay apparatus, the temperature is that at which an assay for an analyte is conducted. The temperature for an assay is dependent on one or more of the nature of the assay, the nature of the assay reagents, and the nature of the analyzer, for example. For assays involving binding members, the medium is incubated at a temperature and for a time sufficient for binding of various components of the reagents and binding of analyte in a sample to occur. Moderate temperatures are normally employed for carrying out the method and usually constant temperature. In some examples, incubation temperatures range from about 5° C. to about 99° C., or from about 15° C. to about 70° C., or about 20° C. to about 45° C., for example.

The duration of the mixing is the duration for which mixing is conducted on a particular mixing device. The duration of mixing is dependent on one or more of the nature of the mixing device, the nature of the composition, and the nature of the container, for example. In some examples, for a mixing device that is part of an assay apparatus, the duration of mixing is that at which an assay for an analyte is conducted. The duration of mixing for an assay is dependent on one or more of the nature of the assay and the nature of the assay reagents, for example. For assays involving binding members, the medium is mixed for a time sufficient for binding of various components of the reagents and binding of analyte in a sample to occur. The time period for the mixing, in some examples, is about 0.2 seconds to about 24 hours, or about 1 second to about 6 hours, or about 2 seconds to about 1 hour, or about 1 minute to about 15 minutes. It should be noted that the duration of mixing prior to the measurement of a second absorbance is often greater than the duration of mixing prior to the measurement of a first absorbance. In some examples, duration of mixing prior to the measurement of a second absorbance is greater than the duration of mixing prior to the measurement of a first absorbance by at least about 0.5 seconds, or at least about 0.75 seconds, or at least about 1 second.

After measurement of the first absorbance and the second absorbance, a ratio of the first absorbance to the second absorbance is determined and a ratio less that about 1 or outside the range of 0.95 to 1.05, or 0.96 to 1.04, or 0.97 to 1.03 indicates that the ability of the test mixing device to mix a reaction mixture at the predetermined intensity level and duration is not adequate. The phrase "less than about 1" means 1±0.05, or 1±0.04, or 1±0.03, or 1±0.02, or 1±0.01, or 1. If inadequate mixing is determined, then reaction results such as, for example, assay results, should not be trusted until mixing is improved by repairing or replacing the test mixing device or by adjusting the mixing intensity level and/or duration of the mixing using the test mixing device.

General Description of Assays

As mentioned above, one area of application of the compositions and methods in accordance with the principles described herein is apparatus for conducting assays for the determination of the presence and/or amount of one or more analytes in a sample to be analyzed. The assay methods usually involve a sample suspected of containing an analyte, which is combined in an assay medium with reagents for carrying out the assay. Assay reagents can include a binding partner for the analyte and one or more other binding partners depending on one or more of the nature of the assay, the nature of the analyte, and the nature of other assay reagents, for example. One or more of the reagents may be part of a signal producing system where at least one of the reagents can be labeled. The reagents are chosen such that a signal is obtained from a label in relation to the presence or amount of analyte in the sample. The assay can be performed either without separation (homogeneous) or with separation (heterogeneous) of any of the assay compounds or products. Assays can be competitive or non-competitive.

Immunoassays may involve labeled or non-labeled reagents. Immunoassays involving non-labeled reagents usually comprise the formation of relatively large complexes involving one or more antibodies prepared from immunogenic conjugates in accordance with the principles described herein. Such assays include, for example, immunoprecipitin and agglutination methods and corresponding light scattering techniques such as, e.g., nephelometry and turbidimetry, for the detection of antibody complexes. Labeled immunoassays include, but are not limited to, chemiluminescence immunoassays, enzyme immunoassays, fluorescence polarization immunoassays, radioimmunoassays, inhibition assays, induced luminescence assays, and fluorescent oxygen channeling assays, for example. All of the above assays generally involve at least one step in which one or more reagents are mixed.

Homogeneous immunoassays are exemplified by the EMIT® assay (Siemens Healthcare Diagnostics Inc., Deerfield, Ill.) disclosed in Rubenstein, et al., U.S. Pat. No. 3,817,837, column 3, line 6 to column 6, line 64; immunofluorescence methods such as those disclosed in Ullman, et al., U.S. Pat. No. 3,996,345, column 17, line 59, to column 23, line 25; enzyme channeling immunoassays ("ECIA") such as those disclosed in Maggio, et al., U.S. Pat. No. 4,233,402, column 6, line 25 to column 9, line 63; the fluorescence polarization immunoassay ("FPIA") as disclosed, for example, in, among others, U.S. Pat. No. 5,354,693; and enzyme immunoassays such as the enzyme linked immunosorbant assay ("ELISA"). Exemplary of heterogeneous assays are the radioimmunoassay, disclosed in Yalow, et al., J. Clin. Invest. 39:1157 (1960). The relevant portions of the above disclosures are all incorporated herein by reference.

Other enzyme immunoassays are the enzyme modulate mediated immunoassay ("EMMIA") discussed by Ngo and Lenhoff, FEBS Lett. (1980) 116:285-288; the substrate labeled fluorescence immunoassay ("SLFIA") disclosed by Oellerich, J. Clin. Chem. Clin. Biochem. (1984) 22:895-904; the combined enzyme donor immunoassays ("CEDIA") disclosed by Khanna, et al., Clin. Chem. Acta (1989) 185:231-240; homogeneous particle labeled immunoassays such as particle enhanced turbidimetric inhibition immunoassays ("PETINIA"), particle enhanced turbidimetric immunoassay ("PETIA"), for example.

Other assays include the sol particle immunoassay ("SPIA"), the disperse dye immunoassay ("DIA"); the metalloimmunoassay ("MIA"); the enzyme membrane immunoassays ("EMIA"); luminoimmunoassays ("LIA"); for example. Other types of assays include immunosensor assays involving the monitoring of the changes in the optical, acoustic and electrical properties of the present conjugate upon the binding of EDDP analyte. Such assays include, for example, optical immunosensor assays, acoustic immunosensor assays, semiconductor immunosensor assays, electrochemical transducer immunosensor assays, potentiometric immunosensor assays, amperometric electrode assays.

The sample to be analyzed is one that is suspected of containing one or more analytes. The sample is preferably from a mammalian subject, e.g., human or other animal species and include biological fluids such as whole blood, serum, plasma, sputum, lymphatic fluid, semen, vaginal mucus, feces, urine, spinal fluid, saliva, stool, cerebral spinal fluid, tears, mucus, for example; biological tissue such as hair, skin, sections or excised tissues from organs or other body parts; for example. In many instances, the sample is whole blood, plasma or serum.

The sample can be prepared in any convenient medium. Conveniently, the sample may be prepared in an assay medium, which is discussed more fully hereinbelow. In some instances a pretreatment may be applied to the sample such as, for example, to lyse blood cells. In some examples, such pretreatment is performed in a medium that does not interfere subsequently with an assay.

Kits Comprising Reagents for Conducting the Methods

Components in compositions in accordance with the principles described herein may be present in a kit useful for conveniently performing methods in accordance with the principles described herein. In some embodiments a kit comprises in packaged combination an organic dye and a density-enhancing material. The kit may further include other reagents for performing the method such as, for example, one or more buffers and one or more preservatives. The components may each be in separate containers or various components can be combined in one or more containers depending on the cross-reactivity and stability of the components.

The relative amounts of the various components in the kits can be those necessary to achieve the desired amounts of the components in a composition in accordance with the principles described herein. Under appropriate circumstances one or more of the components in the kit can be provided in a dry state. The kit can further include a written description of a method utilizing reagents that include a conjugate in accordance with the principles described herein.

The phrase "at least" as used herein means that the number of specified items may be equal to or greater than the number recited. Except as otherwise defined, the phrase "about" as used herein means that the number recited may differ by plus or minus 10%; for example, "about 5" means a range of 4.5 to 5.5.

The designation "first" and "second" is completely arbitrary and is not meant to suggest any order or ranking among items identified or any order of addition of items identified in the present methods.

The following discussion is directed to specific examples in accordance with the principles described herein by way of illustration and not limitation; the specific examples are not intended to limit the scope of the present disclosure and the appended claims. Numerous modifications and alternative compositions, methods, and systems may be devised without departing from the spirit and scope of the present disclosure.

EXAMPLES

Unless otherwise indicated, materials in the experiments below may be purchased from the Sigma-Aldrich Chemical Corporation, St. Louis Mo. Parts and percentages disclosed herein are by weight to volume unless otherwise indicated.

Definitions mg=milligram
g=gram(s)
mL=milliliter(s)
μL=microliter(s)
° C.=degrees Centigrade
min=minute(s)
sec=second(s)
w/v=weight to volume Preparation and Use of Composition with Erioglaucine and Sucrose A composition was prepared by combining the components set forth below to achieve the concentrations specified. The composition was composed of 0.14 mg/mL of Erioglaucine (CAS #384404509), 1.25 M sucrose, 20 mM sodium acetate (pH=5.4), 1 mM EDTA, 1% PROCLIN® 950 and 0.1 mg/mL neomycin sulfate. The composition had a density of 1.17 g/mL and a viscosity of 4.2 centipoise.

The composition was employed to assess the mixing adequacy of a test mixing device on a DIMENSION® VISTA® Intelligent Lab analyzer (Siemens Healthcare Diagnostics Inc., Tarrytown N.Y. To a cuvette (0.15 mL) was dispensed 145 μL of water. The composition from above (5 μL) was then dispensed to the cuvette such that the composition formed a layer below a layer of the water in the cuvette. The layers in the cuvette were subjected to mixing using the test mixing device at standard mixing intensity at a temperature of 37° C. for a period of 0.5 sec. After such mixing, a first absorbance from the mixture was measured at 600 nm. The absorbance was measured at a point just above the interface of the top and the bottom layers.

After the above measurement of the absorbance of the mixture in the cuvette, the layers in the cuvette were subjected to mixing using a control mixing device at standard mixing intensity at a temperature of 37° C. for a period of 1 sec. The control mixing device and conditions were known to achieve adequate mixing of the layers in the cuvette. After such mixing, a second absorbance from the mixture was measured at 600 nm. After measurement of the first absorbance and the second absorbance, a ratio of the first absorbance to the second absorbance was determined to be 0.75. This indicated that the mixing on the test mixing device was inadequate and unsuitable for assay processing and thus, the test mixing device needs repair or replacement or the mixing intensity level and/or duration needs to be increased to determine whether adequate mixing can be achieved with the test mixing device.

Preparation and Use of Composition with Erioglaucine and Glycerol

A composition was prepared by combining the components set forth below to achieve the concentrations specified. The composition was composed of 0.14 mg/mL of Erioglaucine (CAS #384404509), 50% (w/v) glycerol, 20 mM sodium acetate (pH=5.4), 1 mM EDTA, 1% PROCLIN® 950 and 0.1 mg/mL neomycin sulfate. The density of the composition is 1.1 g/mL and the viscosity is 3.9 centipoise.

The composition was employed to assess the mixing adequacy of a test mixing device on a DIMENSION® VISTA® Intelligent Lab analyzer (Siemens Healthcare Diagnostics Inc.). To a cuvette (0.15 mL) was dispensed 145 μL of water. The composition from above (5 μL) was then dispensed to the cuvette such that the composition formed a layer below a layer of the water in the cuvette. The layers in the cuvette were subjected to mixing using the test mixing device at standard mixing intensity at a temperature of 37° C. for a period of 0.5 sec. After such mixing, a first absorbance from the mixture was measured at 600 nm. The absorbance was measured at a point just above the interface of the top and the bottom layers.

After the above measurement of the absorbance of the mixture in the cuvette, the layers in the cuvette were subjected to mixing using a control mixing device at standard mixing intensity at a temperature of 37° C. for a period of 1 sec. The control mixing device and conditions were known to achieve adequate mixing of the layers in the cuvette. After such mixing, a second absorbance from the mixture was measured at 600 nm. After measurement of the first absorbance and the second absorbance, a ratio of the first absorbance to the second absorbance was determined to be 0.75. This indicated that the mixing on the test mixing device was inadequate and unsuitable for assay processing and thus, the test mixing device needs repair or replacement or the mixing intensity level and/or duration needs to be increased to determine whether adequate mixing can be achieved with the test mixing device.

Preparation and Use of Composition with Erioglaucine and Fructose

A composition is prepared and comprises 0.14 mg/mL of Erioglaucine (CAS #384404509) and 1.25 M fructose. The composition is employed as described above to assess the mixing adequacy of a test mixing device on a DIMENSION® VISTA® Intelligent Lab analyzer (Siemens Healthcare Diagnostics Inc.). The mixing of the layers is determined to be inadequate and unsuitable for assay processing and thus, the test mixing device needs repair or replacement or the mixing intensity level and/or duration needs to be increased to determine whether adequate mixing can be achieved with the test mixing device.

Preparation and Use of Composition with Malachite Green and Sucrose

A composition is prepared and comprises 0.15 mg/mL of malachite green and 1.25 M sucrose. The composition is employed as described above to assess the mixing adequacy of a test mixing device on a DIMENSION® VISTA® Intelligent Lab analyzer (Siemens Healthcare Diagnostics Inc.). The mixing of the layers is determined to be inadequate and unsuitable for assay processing and thus, the test mixing device needs repair or replacement or the mixing intensity level and/or duration needs to be increased to determine whether adequate mixing can be achieved with the test mixing device.

Preparation and Use of Composition with Ponceau S and Trehalose

A composition is prepared and comprises 0.14 mg/mL of Ponceau S and 1.25 M trehalose. The composition is employed as described above to assess the mixing adequacy of a test mixing device on a DIMENSION® VISTA® Intelligent Lab analyzer (Siemens Healthcare Diagnostics Inc.). The mixing of the layers is determined to be inadequate and unsuitable for assay processing and thus, the test mixing device needs repair or replacement or the mixing intensity level and/or duration needs to be increased to determine whether adequate mixing can be achieved with the test mixing device.

All publications and patent applications cited in this specification are herein incorporated by reference as if each individual publication or patent application were specifically and individually indicated to be incorporated by reference.

It should be understood that the above-described examples are merely illustrative of some of the many specific examples that represent the principles described herein. Clearly, those skilled in the art can readily devise numerous other arrangements without departing from the scope as defined by the following claims.

What is claimed is:

1. A composition consisting of an aqueous solution of an organic dye of molecular weight in the range of about 300 to about 1,000 Dalton and a density-enhancing material wherein an amount of the density-enhancing material in the aqueous solution is sufficient to achieve a density of about 1.0 to about 1.3 g/mL and wherein the composition has a viscosity of about 3.5 to about 5.0 centipoise, wherein the organic dye is
   an aromatic azo dye, or
   a triarlymethane dye, or is
   selected from the group consisting of Erioglaucine, Ponceau S, Allura Red, Acid Red, Malachite Green, and Amaranth.

2. The composition according to claim 1 wherein the density-enhancing material is a polyhydroxy compound, or
   a polyol, a monosaccharide or a disaccharide, or is
   selected from the group consisting of sucrose, fructose, trehalose and a mixture of two or more thereof.

3. The composition according to claim 1 further consisting of one or both of a buffer and a preservative.

4. A method of assessing the adequacy of a test mixing device to mix a reaction mixture, the method comprising:
   subjecting a layer of water adjacent a layer of the composition of claim 1 in a container to mixing using the test mixing device at a predetermined level of intensity and duration and measuring a first absorbance from the mixture at a predetermined wavelength;
   subjecting a layer of water adjacent a layer of the composition of claim 1 in a container to mixing using a control mixing device at a level of intensity and duration that maximizes mixing of the mixture and measuring a second absorbance from the mixture at the predetermined wavelength; and
   determining a ratio of the first absorbance to the second absorbance wherein a ratio outside the range of 0.95 to 1.05 indicates that the ability of the test mixing device to mix a reaction mixture at the predetermined intensity level and duration is not adequate.

5. The composition according to claim 1, wherein the organic dye is an aromatic azo dye and wherein the density-enhancing material is a monosaccharide or disaccharide wherein the amount of monosaccharide or disaccharide in the aqueous solution is sufficient to achieve a density of about 1.1 to about 1.2 g/mL and wherein the composition has a viscosity of about 3.5 to about 5.0 centipoise.

6. The composition according to claim 5 wherein the organic dye is a triarylmethane azo dye or a fused aryl ring azo dye.

7. The composition according to claim 5 wherein the monosaccharide or disaccharide is selected from the group consisting of sucrose, fructose, trehalose and a mixture of two or more thereof.

8. The composition according to claim 5 further consisting of one or both of a buffer and a preservative.

9. A method of assessing the adequacy of a test mixing device to mix a reaction mixture, the method comprising:
   subjecting a layer of water above a layer of the composition of claim 6 in a container to mixing using the test mixing device at a predetermined intensity level and duration and measuring a first absorbance from the mixture at a predetermined wavelength, subjecting a layer of the composition of claim 6 adjacent a layer of water in a container to mixing using a control mixing device at an intensity level and duration that maximizes mixing of the mixture and measuring a second absorbance from the mixture at the predetermined wavelength; and determining a ratio of the first absorbance to the second absorbance wherein a ratio outside the range of 0.95 to 1.05 indicates that the ability of the test mixing device to mix a reaction mixture at the predetermined level of intensity and duration is not adequate.

10. The method according to claim 9 wherein a ratio less than 0.95 indicates that the ability of the test mixing device to mix a reaction mixture at the predetermined intensity level and duration is not adequate.

11. The method according to claim 9 wherein the test mixing device is part of an automated analyzer.

12. The method according to claim 9 wherein the organic dye is selected from the group consisting of Ponceau S, Allura Red, Acid Red, and Amaranth and the density-enhancing material is selected from the group consisting of sucrose, fructose, trehalose and mixtures of two or more thereof.

* * * * *